United States Patent
Wilson

(12) 
(10) Patent No.: US 9,414,949 B2
(45) Date of Patent: Aug. 16, 2016

(54) SHOE INTERFACED ANKLE SUPPORT APPARATUS

(71) Applicant: Tyrone Wilson, Washington, NC (US)

(72) Inventor: Tyrone Wilson, Washington, NC (US)

( * ) Notice: Subject to any disclaimer, the term of this patent is extended or adjusted under 35 U.S.C. 154(b) by 177 days.

(21) Appl. No.: 14/198,782

(22) Filed: Mar. 6, 2014

(65) Prior Publication Data

US 2015/0250632 A1  Sep. 10, 2015

(51) Int. Cl.
*A61F 5/00* (2006.01)
*A61F 5/01* (2006.01)

(52) U.S. Cl.
CPC .................... *A61F 5/0102* (2013.01)

(58) Field of Classification Search
CPC ......... A61F 5/111; A61F 5/108; A61F 5/113; A61F 5/0127
USPC .................... 602/16, 23–28, 60–62
See application file for complete search history.

(56) References Cited

U.S. PATENT DOCUMENTS

| 4,313,433 | A |   | 2/1982  | Cramer |
| 4,547,981 | A |   | 10/1985 | Thais et al. |
| 4,621,648 | A |   | 11/1986 | Ivany |
| 4,869,267 | A |   | 9/1989  | Grim et al. |
| 4,878,505 | A | * | 11/1989 | Thanner ................ A61F 5/0111 128/882 |
| 5,016,623 | A |   | 5/1991  | Krahenbuhl |
| 5,092,319 | A |   | 3/1992  | Grim |
| 5,430,960 | A |   | 7/1995  | Richardson |
| 5,501,659 | A |   | 3/1996  | Morris et al. |
| 6,126,625 | A | * | 10/2000 | Lundberg .............. A61F 5/0118 602/27 |
| 7,370,442 | B2 |  | 5/2008  | Jung et al. |
| 2004/0034316 | A1 | * | 2/2004 | Castro ................... A61F 5/0111 602/27 |
| 2005/0038365 | A1 | * | 2/2005 | Scott ..................... A61F 5/0113 602/23 |
| 2008/0082034 | A1 | * | 4/2008 | Wilkerson .............. A61L 15/07 602/27 |
| 2012/0004587 | A1 |   | 1/2012 | Nickel et al. |
| 2012/0059299 | A1 | * | 3/2012 | Clements ............. A61F 5/0127 602/27 |

* cited by examiner

*Primary Examiner* — Michael Brown
(74) *Attorney, Agent, or Firm* — Dale J. Ream

(57) ABSTRACT

A shoe-interfaced ankle support apparatus includes a leg support member having a side wall defining an open top and open bottom configured to be worn on the user's lower leg. The support apparatus includes a primary foot sling having first and second ends coupled to the side wall of the leg support portion adjacent the closed bottom, the foot sling having a length configured to extend loosely across the open bottom of the leg support portion so as to selectively cradle the foot of the user while in a shoe. A shoe interface member includes a proximal end coupled to the side wall of the leg support portion adjacent the open bottom and extending away, the shoe interface member having a plurality of apertures configured to register with respective holes of the shoe's lace portion and to receive the shoelace of the shoe therethrough.

17 Claims, 7 Drawing Sheets

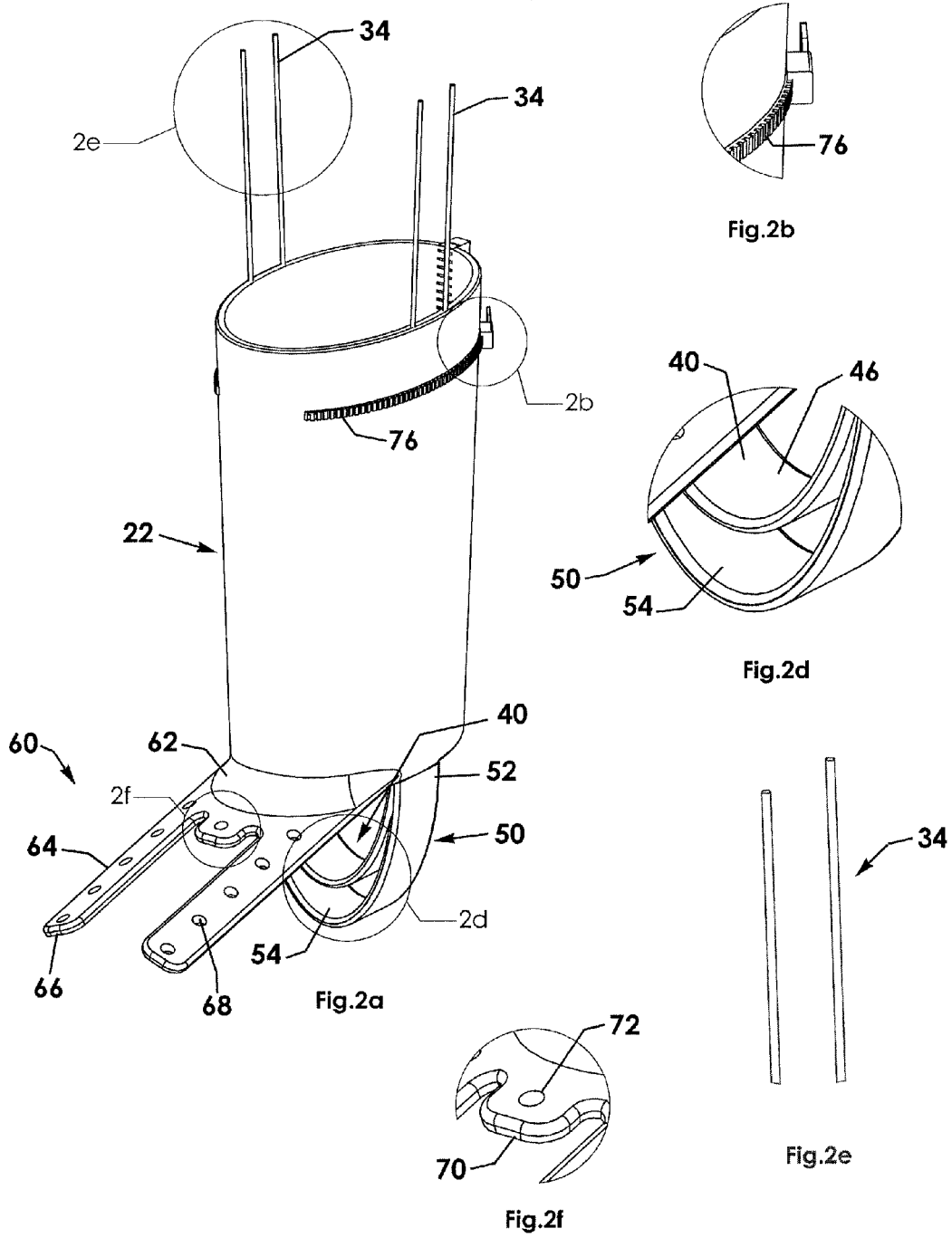

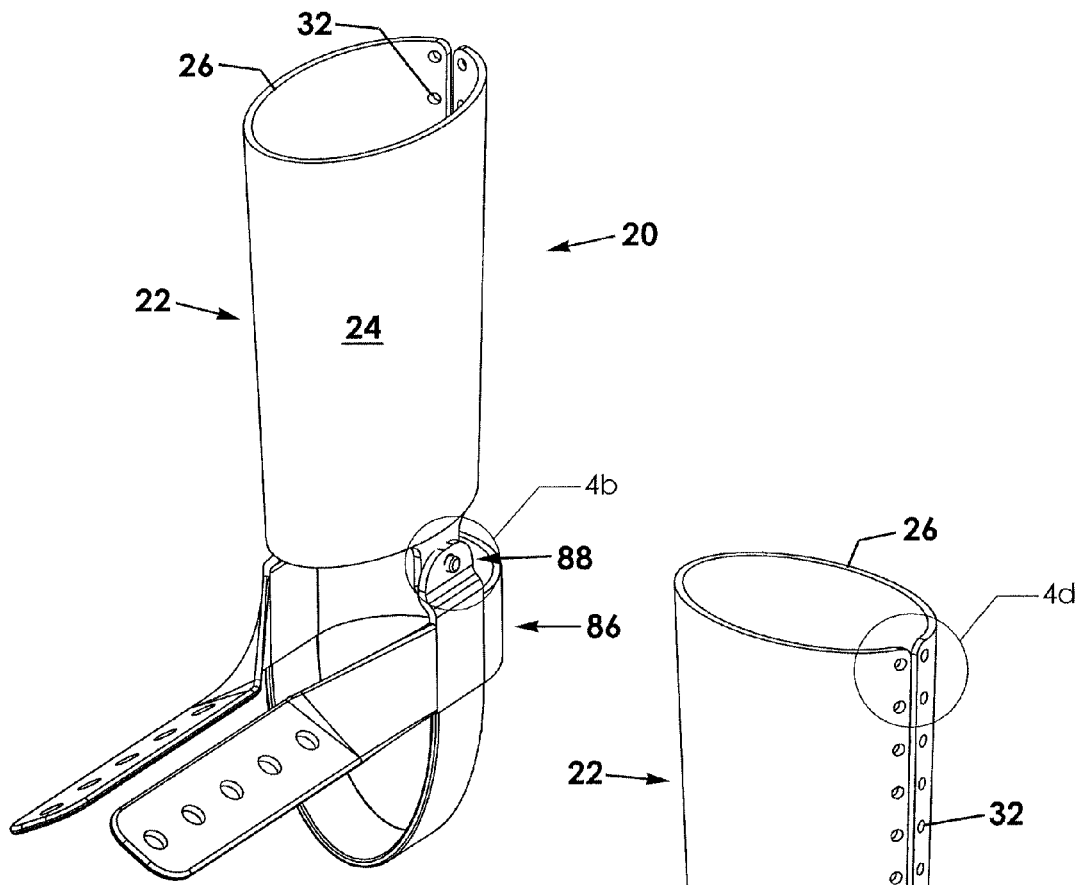
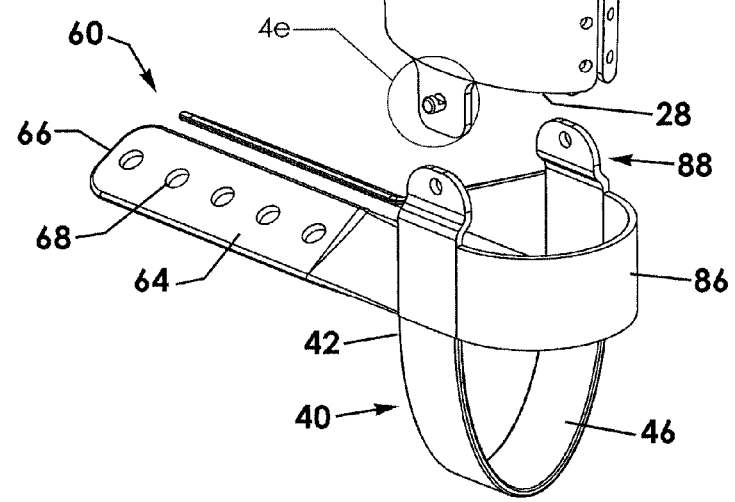

SHOE INTERFACED ANKLE SUPPORT APPARATUS

BACKGROUND OF THE INVENTION

This invention relates generally to ankle braces and, more particularly, to an ankle and leg support apparatus that is worn on the lower leg of a person and which interfaces with the shoe lace portion and shoe laces of any lace-type shoe.

A sprained ankle is a common injury to the ligaments in the ankle region of a persons lower leg and foot. Sometime called a sprain, a twisted ankle, a rolled ankle, or the like, the condition is caused by the partial tearing of ligaments of the ankle. A sprained ankle is usually caused when a person's foot "rolls" or collapses due to an awkward step or when an uneven ground surface urges the foot to essentially fold over when weight is applied over the foot while walking or running.

Various devices and treatments have been proposed in the art for enhancing healing of an ankle sprain or simply for minimizing the pain of the injury. For instance, elastic wraps and braces are beneficial in that they provide a compression force that gives a person reassurance while walking. Of course, crutches may be used by a person with a sprained ankle so as to eliminate any weight-bearing on the affected ankle. Although assumably effective for their intended purposes, the existing devices and proposals do not provide an apparatus that provides compression to the lower leg, sling cradling of a person's foot to lessen its weight bearing, and the ability to tighten the compression by tightening the laces of a shoe to which the apparatus is interfaced.

Therefore, it would be desirable to have a shoe-interfaced ankle support apparatus that may be worn about the lower leg of a person with a sprained ankle and which cradles the person's foot inside a shoe. Further, it would be desirable to have a shoe-interfaced ankle support apparatus that is coupled to the lace portion of a lace-up type shoe and can be tightened with the shoe laces.

SUMMARY OF THE INVENTION

A shoe-interfaced ankle support apparatus according to the present invention includes a leg support member having a continuous side wall defining an open top and open bottom configured to be worn on the user's lower leg. The support apparatus includes a primary foot sling having opposed first and second ends coupled to the side wall of the leg support portion adjacent the closed bottom, the foot sling having a length configured to extend loosely across the open bottom of the leg support portion so as to selectively receive and cradle the foot of the user. A shoe interface member includes a proximal end operatively coupled to the side wall of the leg support portion adjacent the open bottom and extending away from the side wall, the shoe interface member having a plurality of spaced apart apertures configured to register with respective holes of the lace portion of the shoe and to receive the shoelace of the shoe therethrough.

Therefore, a general object of this invention is to provide an ankle support apparatus that is worn about the foot and lower leg of a person and that interfaces with the shoe laces of any lace-type shoe.

Another object of this invention is to provide an ankle support apparatus, as aforesaid, that can be increasingly tightened about a person's ankle by lacing the shoe tighter.

Still another object of this invention is to provide an ankle support apparatus, as aforesaid, that can be increasingly tightened about a person's lower leg by tightening the leg support member.

Yet another object of this invention is to provide an ankle support apparatus, as aforesaid, that cradles a person foot and ankle in a foot sling when the apparatus is worn and the apparatus is interfaced with a shoe.

A further object of this invention is to provide an ankle support apparatus, as aforesaid, that is easy for a user to wear and to lace to a regular lace-type shoe.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 1b is an isolated view on an enlarged scale taken from FIG. 1a;

FIG. 1c is an isolated view on an enlarged scale taken from FIG. 1a;

FIG. 2a is a perspective view of a shoe-interfaced ankle support apparatus according to another embodiment of the present invention with a primary pocket fastener in a closed configuration;

FIG. 2b is an isolated view on an enlarged scale taken from FIG. 2a;

FIG. 2d is an isolated view on an enlarged scale taken from FIG. 2a;

FIG. 2e is an isolated view on an enlarged scale taken from FIG. 2a;

FIG. 2f is an isolated view on an enlarged scale taken from FIG. 2a;

FIG. 2g is an isolated view on an enlarged scale taken from FIG. 2a;

FIG. 2h is a perspective view from another angle as in FIG. 2a;

FIG. 4a is a perspective view of a shoe-interfaced ankle support apparatus according to another embodiment of the present invention FIG. 4b is an isolated view on an enlarged scale taken from FIG. 4a;

FIG. 4c is an exploded view of the ankle support apparatus as in FIG. 4a;

FIG. 4d is an isolated view on an enlarged scale taken from FIG. 4a; and

FIG. 4e is an isolated view on an enlarged scale taken from FIG. 4a.

DESCRIPTION OF THE PREFERRED EMBODIMENT

A shoe-interfaced ankle support apparatus according to a preferred embodiment of the present invention will now be described with reference to FIGS. 1a to 4e. The ankle support apparatus 10 includes a leg support member 20, a primary foot sling 40, and a shoe interface member 60.

Figure 1A:
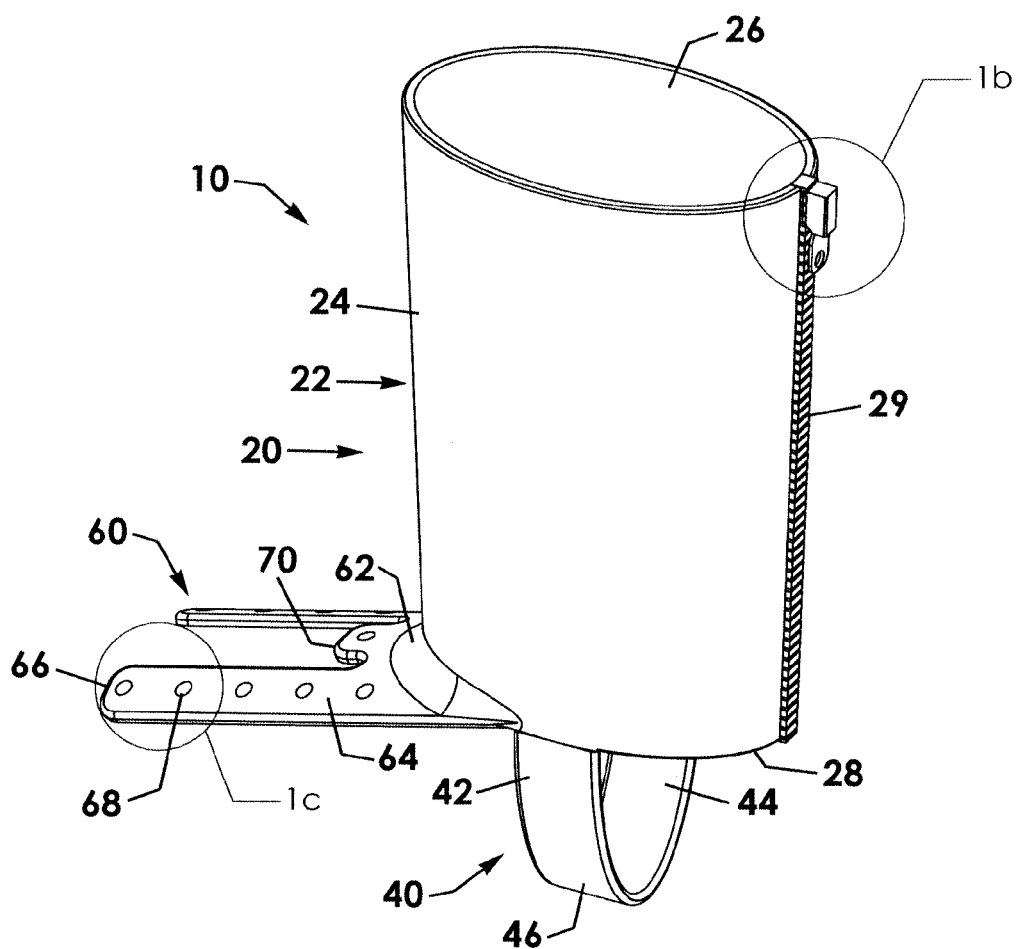
FIG. 1a is a perspective view of a shoe-interfaced ankle support apparatus according to a preferred embodiment of the present invention with a sleeve fastener in a closed configuration.
Figure 1B:
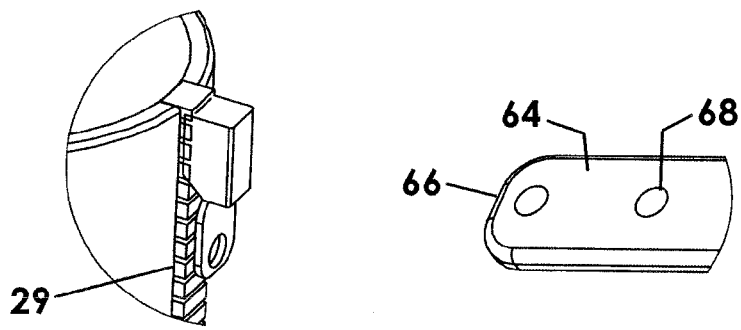
Figure 1C:
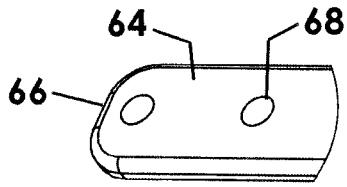

The leg support member 20 may include a sleeve 22 having a continuous side wall 24 that defines an open top 26, open bottom 28, and open interior space between the ends (FIG. 1a). In one embodiment, the sleeve 22 may be constructed of an elastic material and is configured to be worn on the lower leg of a person seeking relief from a sprained ankle. As with traditional ankle or leg support products, the sleeve 22 may be pulled on over a person's foot and pulled upwardly to the lower leg (e.g. calf) area. The sleeve 22 is configured to provide compression to an affected area and give reassurance of support to the wearer.

Figure 1D:
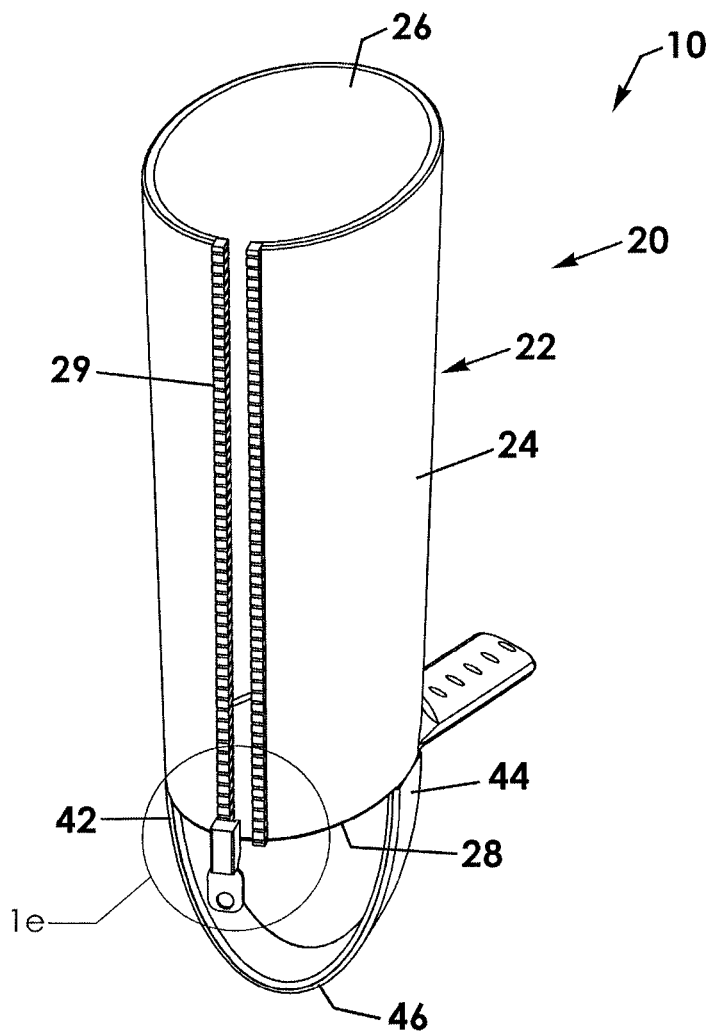
FIG. 1d is a perspective view from another angle of the ankle support apparatus as in FIG. 1a with the sleeve fastener in a released configuration.
Figure 1E:
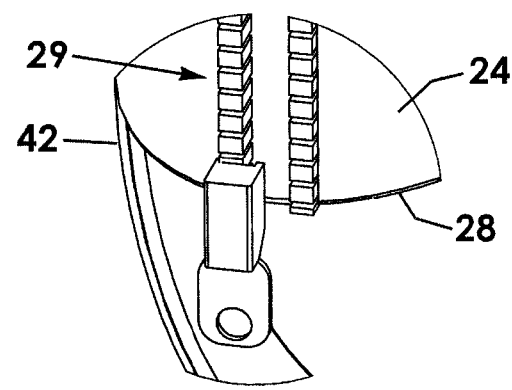
FIG. 1e is an isolated view on an enlarged scale taken from FIG. 1d.

In one embodiment, the sleeve 22 may include first and second edges that are normally separated from one another so as to define an open side (FIG. 1d). The first and second edges, however, may be selectively coupled together with a sleeve fastener 29 such as a zipper (FIG. 1a). Specifically, the sleeve 22 is movable between a closed configuration (FIG. 1a) when the sleeve fastener 29 is fully engaged and an open configuration (FIG. 1d) when the sleeve fastener 29 is fully released. In use, the sleeve fastener 29 may be released and the sleeve side wall 24 wrapped around a person's lower leg and then the sleeve fastener 29 reengaged. Although the sleeve fastener 29 is preferably a zipper, the sleeve fastener 29 may also include a hook and loop combination, clasp, snap combination, or other suitable fastener.

Figure 4B:
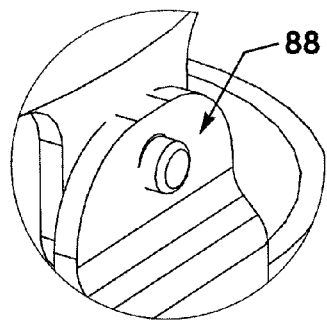
Figure 4D:
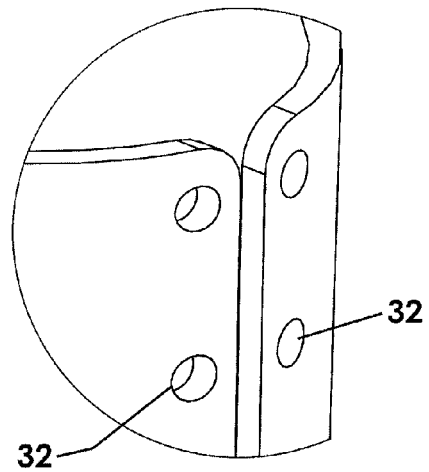
Figure 4E:
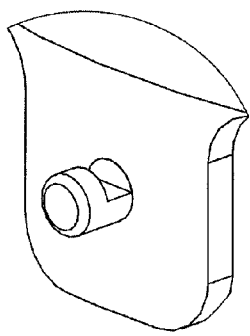

In one embodiment, the sleeve fastener 29 may include a lacing arrangement. More particularly, the side wall 24 of the sleeve 22 adjacent the first and second side edges may define a plurality of lace holes 32 spaced apart between the open top 26 and open bottom 28 thereof (FIGS. 4a and 4c). A shoe lace (not shown) may then laced through respective holes and tightened as desired by the user in a manner similar to lacing up a boot, roller skate, or the like. In this manner, the leg support member 20 may be tightened about a user's leg to a desired tightness and compression.

Figure 2H:
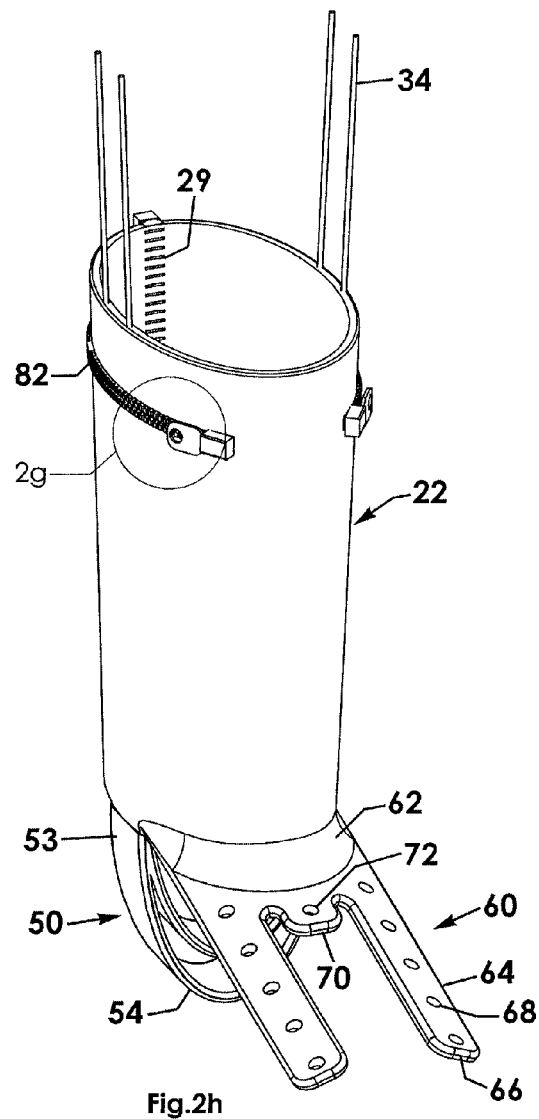
Figure 2G:
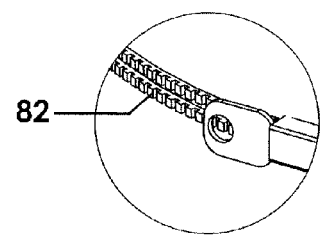
Figure 2C:
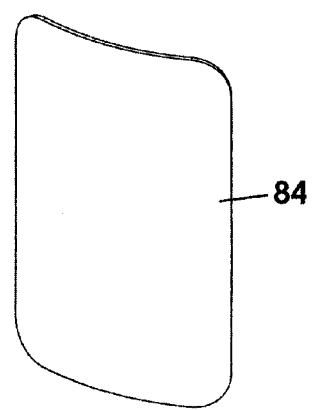
FIG. 2c is a perspective view of a padded panel.

In another embodiment, the sleeve 22 may be tightened using an internal network of cords 34. More particularly, the sleeve fastener 29 includes at least a pair of cords 34 embedded in a network arrangement within an interior area of the sleeve 22 and having free ends that extend upwardly from the sleeve 22 adjacent the open top 26 thereof (FIG. 2a). For instance, the cords 34 may be situated in a generally spiral arrangement throughout the side wall 24 of the sleeve 22 so as to tighten the sleeve 22 when worn on a user's leg and the cords 34 are pulled upwardly.

The primary foot sling 40 may include opposed first 42 and second 44 ends operatively coupled to opposed points of the side wall 24 of the leg support member 20, respectively, adjacent the open bottom 28. In one embodiment, the foot sling ends may be coupled directly and permanently to the sleeve 22 (FIG. 1a). In another embodiment, the ends of the primary foot sling 40 may be coupled to an ankle/leg interface 88 that is situated intermediate the primary foot sling 40 and sleeve 22, as will be described in more detail later (FIG. 4a).

The primary foot sling 40 includes a length and configuration so as to extend loosely between the opposed points of attachment to the side wall 24 of the leg support member 20. In other words, the primary foot sling 40 includes a generally U-shaped cradle portion 46 that hangs downwardly from the leg support member 20 and into a user's shoe so as to cradle a foot. The primary foot sling 40 may be constructed of an elastic material that is configured to receive and cradle a heel portion of a user's foot. In use, the leg support member 20 may be securely worn about the lower leg portion of a user's leg so that the primary foot sling 40 forms a cradle for the user's foot. When the user puts on a shoe, the cradle is configured to remove or relieve the normal weight or force of the foot upon the sole of the shoe.

In another embodiment, a secondary foot sling 50 is situated below the primary foot sling 40 and configured to enhance the support of a user's foot (FIG. 2a). More particularly, the secondary foot sling 50 includes opposed first 52 and second 53 ends coupled to opposed points of the side wall 24 of the leg support member 20, the secondary foot sling 50 having a secondary cradle portion 54 configured to extend loosely across the open bottom 28 thereof in a cradle configuration manner substantially similar to the primary foot sling 40 described above. In one embodiment, the secondary foot sling 50 may have a less flexible construction so as not to stretch when receiving the weight of a user's foot. In other words, the secondary foot sling 50 may be designed as a stop or limit to the downward movement of a user's foot.

The shoe interface member 60 provides the means for coupling the ankle support apparatus 10 to a shoe (FIG. 1a). In use, the ankle support apparatus 10 may be selectively and releasably coupled to any lace-type shoe as will become apparent below. The shoe interface member 60 includes a proximal end 62 operatively coupled to the side wall 24 of the leg support member 20 adjacent the open bottom 28 thereof. In other words, the shoe interface member 60 may be directly coupled to the sleeve 22 or, in some embodiments, there may be intermediate structures connecting to the two. The shoe interface member 60 extends away from the sleeve 22. Namely, the shoe interface member 60 may extend forwardly and generally perpendicular to the upstanding side wall 24 of the leg support member 20 (FIG. 1a). In one embodiment, the shoe interface member 60 may be pivotally coupled to the sleeve 22 so as to move flexibly when being coupled to a particular configuration of a shoe.

The shoe interface member 60 may include a pair of spaced apart interface sections 64 extending away from the proximal end 62 that define a plurality of apertures 68, the pair of interface sections 64 being generally parallel to one another and define a void therebetween. Each interface section 64 includes a terminal or free end 66 displaced from the proximal end 62 of the shoe interface member 60. The shoe interface member 60 is configured such that the plurality of apertures 68 register or line up with the plurality of lace holes on a lace-up type of shoe, thus enabling a shoe lace to be threaded through respective lace holes and apertures 68 in order to couple the shoe interface member 60 to the shoe. In the same manner that a shoe is tightened using its shoe laces, the compression imparted by the shoe interface member 60 may be tightened by tightening the laces. Tightening the laces may also create an upward force by the primary foot sling 40 on the bottom of a user's foot when positioned in a shoe.

In one embodiment, the shoe interface member 60 includes a tongue tab 70 coupled to the proximal end 62 of the shoe interface member 60. The tongue tab 70 is configured to register or line up with a traditional tongue of a lace-up type shoe. The tongue tab 70 may define a through hole 72 configured to receive a shoe lace (not shown) of the shoe so as to enhance the position of the shoe interface member 60 and its secure attachment to the shoe. It is understood that the tongue tab 70 is situated intermediate the pair of interface sections 64 so that a shoe lace may be selectively inserted through respective apertures 68 and through hole 72.

Another embodiment of the shoe-interfaced ankle support apparatus 10 includes a construction substantially similar to that described previously except as specifically noted below. In this embodiment, the sleeve 22 described previously defines a primary pocket. The sleeve also defines a primary slot in communication with the primary pocket and configured to selectively give access to the primary pocket (FIG. 2a). More particularly, a primary pocket fastener 76 may be moved from a closed configuration preventing access to the primary pocket and an open configuration allowing access to the primary pocket. The primary pocket fastener 76 may be a zipper configured to be selectively moved between open and closed configurations, although the primary pocket fastener 76 may also include a hook and loop combination, snap-fit arrangement, clasp, flap, or the like.

A primary padded panel 78 may be positioned in the primary pocket of the sleeve 22 and can be inserted into or removed from the primary pocket through the primary slot described above (FIG. 3a). The primary padded panel 78 is configured to shield a user's lower leg from impact forces, such as may be inexperienced during recreational activities.

Similarly, the sleeve 22 may define a secondary pocket and a secondary slot in communication with the secondary pocket. Likewise, a secondary pocket fastener 82 may be situated at the secondary slot and is movable between open and closed configuration to selectively provide or restrict access thereto (FIG. 2f). A secondary padded panel 84 may also be inserted into or removed from the secondary pocket and, when inserted, enhance protection to a user's lower leg.

In one embodiment, the shoe-interfaced ankle support apparatus 10 includes a heel support member 86 having opposed ends that are operatively coupled to opposed edges, respectively, of the side wall 24 of the leg support member 20 adjacent the open bottom 28 (FIGS. 4a and 4c). The heel support member 86 is configured to extend rearwardly. The heel support member 86 has a generally U-shaped configuration so as to surround the heel of a person's foot when the leg support member 20 is worn about a user's lower leg. The heel support member 86 may be constructed of an elastic material so as to impart compressive force against a user's heel. It is noted that the heel support member 86 is oriented generally perpendicular to the side wall 24 of the leg support member 20. When the leg support member 20 is positioned on a user's lower leg, the primary foot sling 40 cradles a person's foot and the heel support member 86 supports the Achilles tendon of the person's foot.

Figure 3A:
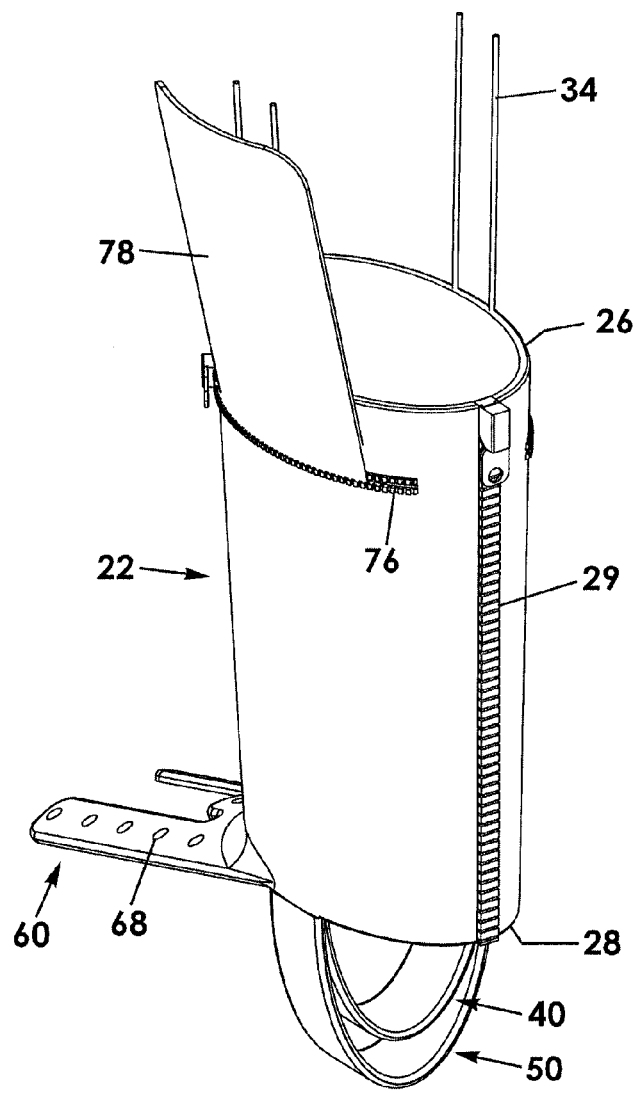
FIG. 3a is a perspective view of the ankle support apparatus as in FIG. 2a from another angle illustrated with a secondary pocket fastener in an open configuration so as to receive a padded panel.

In another embodiment, the shoe-interfaced ankle apparatus 10 includes an ankle/leg interface 88 having at least one first end releasably coupled to the side wall 24 of the leg support member 20 adjacent the open bottom 28 and at least one second end operatively coupled to the primary foot sling 40 and to the shoe interface member 60. The heel support member 86 may also be operatively coupled to the ankle/leg interface 88. In one embodiment, the ankle/leg interface 88 may have opposed first ends coupled to opposed points of the side wall 24 and opposed second ends coupled to the primary foot sling 40 and to the shoe interface member 60 as shown in FIG. 3a. The ankle/leg interface 88 is essentially a linkage between the leg support member 20 ("an upper portion") and the other components of the apparatus 10 ("a lower portion"). Accordingly, the leg support member 20 may be released from the other components and either portion may be utilized without the other. (FIG. 4c).

In use, a person having a sprained ankle first puts on the shoe-interfaced ankle support apparatus 10 by pulling the leg support member 20 over his foot and onto the lower ("calf") portion of his leg. In some embodiments, the leg support member 20 may be loosened by releasing or disengaging the sleeve fastener 29. The leg support member 20 should be oriented on the user's leg such that the shoe interface member 60 extends forwardly. The leg support member 20 should be pulled upwardly on the user's leg until the person's foot is cradled by the primary foot sling 40 and, in some embodiments, engaged by the heel support member 86. Then, the user may insert his foot, including the primary foot sling 40, into a shoe of the lace-up type such that the shoe interface member 60 rests upon the shoe lace portion of the shoe. The shoe laces of the shoe may then be restrung to couple the interface sections to the shoe lace portion as described above. The leg support member 20 may be tightened as described above.

It is understood that while certain forms of this invention have been illustrated and described, it is not limited thereto except insofar as such limitations are included in the following claims and allowable functional equivalents thereof.

The invention claimed is:

1. A shoe-interfaced ankle support apparatus for wear on a lower leg and foot of a user while wearing a shoe having a sole, an upper portion, and a lace portion defining a plurality of holes configured to receive a shoe lace, said shoe-interfaced ankle support apparatus, comprising:
    a leg support member having a continuous side wall defining an open top and open bottom configured to be worn on the user's lower leg;
    a primary foot sling having opposed first and second ends coupled to said side wall of said leg support portion adjacent said closed bottom, said foot sling having a cradle portion having a length configured to extend loosely across said open bottom of said leg support portion so as to selectively receive and cradle the foot of the user, said primary foot sling being constructed of an elastic material;
    a secondary foot sling having opposed first and second ends coupled to said side wall of said leg support portion adjacent said closed bottom, said secondary foot sling having a second cradle portion having a length configured to extend loosely across said open bottom of said leg support portion and is downwardly and concentrically displaced from said primary foot sling so as to limit the downward movement of the person's foot cradled in said primary foot sling;
    a shoe interface member having a proximal end operatively coupled to said side wall of said leg support member adjacent said open bottom and extending away from said side wall, said shoe interface member having a plurality of spaced apart apertures configured to register with respective holes of the lace portion of the shoe and to receive the shoelace of the shoe therethrough;
    wherein said shoe interface member includes a pair of interface sections extending away from said proximal end and defining said plurality of apertures, each interface section having an elongate rectangular configuration only coupled to said side wall by said proximal end, said pair of interface sections being generally parallel to one another and defining a void therebetween.

2. The shoe-interfaced ankle support apparatus as in claim 1, wherein said primary foot sling is operatively coupled to said shoe interface member.

3. The shoe-interfaced ankle support apparatus as in claim 1, wherein said leg support member includes a sleeve configured to surround the lower leg of the user and is constructed of an elastic material that provides compression on the lower leg.

4. The shoe-interfaced ankle support apparatus as in claim 3, wherein said sleeve includes a sleeve fastener extending between said open top and said open bottom and is configured to selectively move said side wall between a closed configuration when said sleeve fastener is engaged and an open configuration when said sleeve fastener is released.

5. The shoe-interfaced ankle support apparatus as in claim 4, wherein said sleeve fastener is one of a hook-and-loop combination and a zipper.

6. The shoe-interfaced ankle support apparatus as in claim 4, wherein said sleeve fastener is a lacing system in which said side wall of said leg support member defines a plurality of spaced apart holes situated between said open top and said open bottom and configured to receive lacing, whereby to selectively tighten said sleeve about the user's lower leg.

7. The shoe-interfaced ankle support apparatus as in claim 4, wherein said sleeve fastener is at least a pair of cords situated in a network arrangement within an interior area of said sleeve, said pair of cords having respective ends extending upwardly of said open top and configured to selectively tighten said sleeve about the user's lower leg.

8. The shoe-interfaced ankle support apparatus as in claim 1, wherein each interface section of said shoe interface member has a terminal end displaced from said proximal end of said shoe interface member.

9. The shoe-interfaced ankle support apparatus as in claim 1, wherein said shoe interface member includes a tongue tab coupled to said proximal end thereof, said tongue tab being positioned to register with a tongue of the shoe and defining a through hole configured to receive the shoe lace therethrough and enhance the selective coupling of the shoe interface member to the shoe.

10. The shoe-interfaced ankle support apparatus as in claim 9, wherein said tongue tab is situated intermediate said pair of interface sections so that the shoe laces may be selectively inserted through respective apertures and through hole.

11. The shoe-interfaced ankle support apparatus as in claim 3, wherein:

said sleeve defines a primary pocket;

said side wall defines an primary slot in communication with said primary pocket;

a primary pocket fastener that is movable between a closed configuration preventing access to said primary pocket and an open configuration allowing access to said primary pocket.

12. The shoe-interfaced ankle support apparatus as in claim 11, further comprising a primary padded panel selectively situated in said primary pocket of said sleeve, said primary padded panel configured to shield a user's lower leg from impact forces.

13. The shoe-interfaced ankle support apparatus as in claim 12, wherein:

said sleeve defines an secondary pocket;

said side wall defines an secondary slot in communication with said secondary pocket;

a secondary fastener that is movable between a closed configuration preventing access to said secondary pocket and an open configuration allowing access to said secondary pocket.

14. The shoe-interfaced ankle support apparatus as in claim 13, further comprising a secondary padded panel selectively situated in said secondary pocket of said sleeve, said secondary padded panel configured to shield a user's lower leg from impact forces.

15. The shoe-interfaced ankle support apparatus as in claim 1, comprising a heel support member operatively coupled to opposed edges of said side wall of said leg support member adjacent said open bottom, said heel support member being configured to extend rearwardly in a generally U-shaped configuration so as to surround a heel of the user's foot when said leg support member is worn on the user's lower leg.

16. The shoe-interfaced ankle support apparatus as in claim 15, comprising an ankle/leg portion interface having at least one first end releasably coupled to said side wall of said leg support member adjacent said open bottom and at least one second end operatively coupled to said primary foot sling and to said shoe interface member and to said heel support member, said ankle/leg portion interface being configured such that said primary foot sling and said shoe interface member and said heel support member are separated from said leg support member when said ankle/leg portion interface is released from said side wall of said leg support member.

17. The shoe-interfaced ankle support apparatus as in claim 1, comprising an ankle/leg portion interface having at least one first end releasably coupled to said side wall of said leg support member adjacent said open bottom and at least one second end operatively coupled to said primary foot sling and to said shoe interface member, said ankle/leg portion interface being configured such that said primary foot sling and said shoe interface member are separated from said leg support member when said ankle/leg portion interface is released from said side wall of said leg support member.

* * * * *